United States Patent [19]

Hernandez

[11] 3,999,547
[45] Dec. 28, 1976

[54] DISPOSABLE DIAPER HAVING FRONT SIDE EDGE SEALING MEANS

[75] Inventor: John Hernandez, East Brunswick, N.J.

[73] Assignee: Colgate-Palmolive Company, New York, N.Y.

[22] Filed: Dec. 29, 1975

[21] Appl. No.: 644,384

[52] U.S. Cl. .............................. 128/284; 128/287
[51] Int. Cl.² ................. A61F 13/16; A41B 13/02
[58] Field of Search ........................... 128/284, 287

[56] References Cited
UNITED STATES PATENTS

| | | | |
|---|---|---|---|
| 2,800,906 | 7/1957 | Hinton | 128/286 |
| 3,386,442 | 6/1968 | Sabee | 128/287 |
| 3,875,943 | 4/1975 | Fischer | 128/287 |
| 3,927,673 | 12/1975 | Taylor | 128/287 |

*Primary Examiner*—Aldrich F. Medbery
*Attorney, Agent, or Firm*—Norman Blumenkopf; Herbert S. Sylvester; Murray M. Grill

[57] ABSTRACT

A disposable diaper comprising a waterproof back sheet, a hydrophobic sheet, and an absorbent pad sandwiched between the back sheet and the face sheet. The diaper is folded to define a box pleated configuration having a central panel, inwardly extending panels and outwardly extending panels with the inner edges of the inwardly extending panels being in abutting relationship. Sealing strips of waterproof material separate from the back sheet are secured on the face sheet. The sealing strips are formed by folding an excess width of the back sheet over the face sheet forming side flap portions, and then cutting the side flap portions free from the back sheet. The sealing strips may be folded inwardly toward the center of the diaper to form fluid catching seals.

19 Claims, 12 Drawing Figures

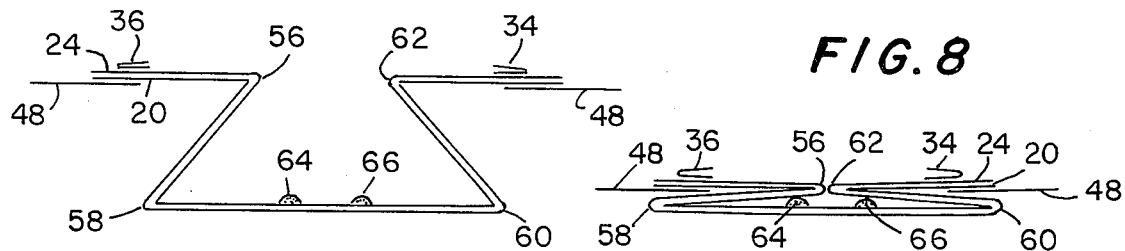
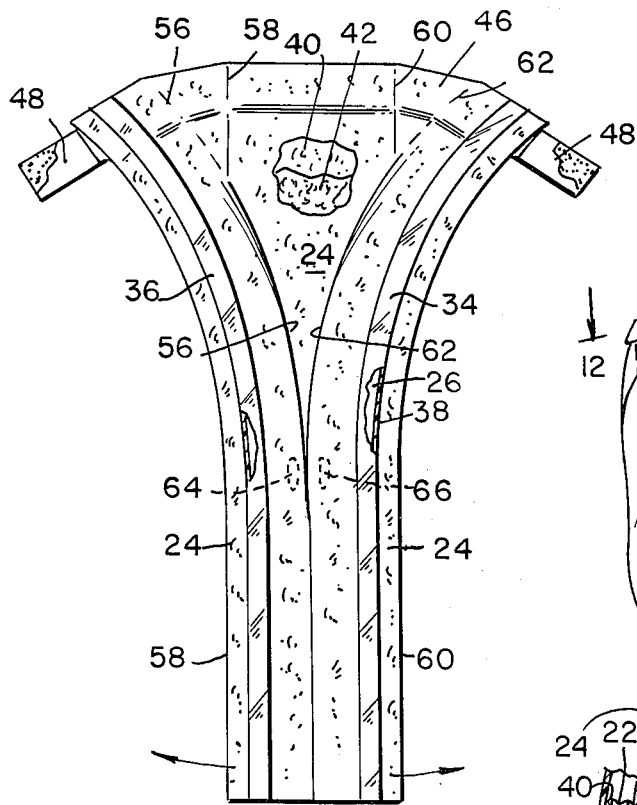
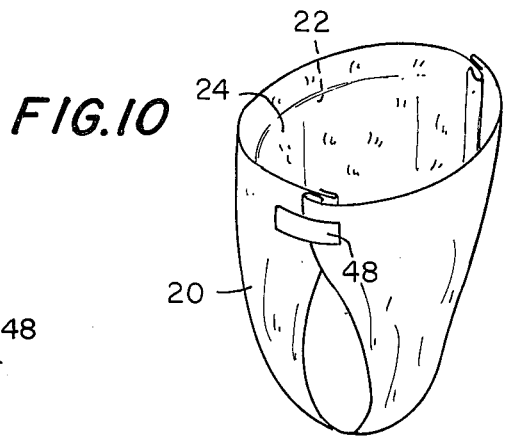
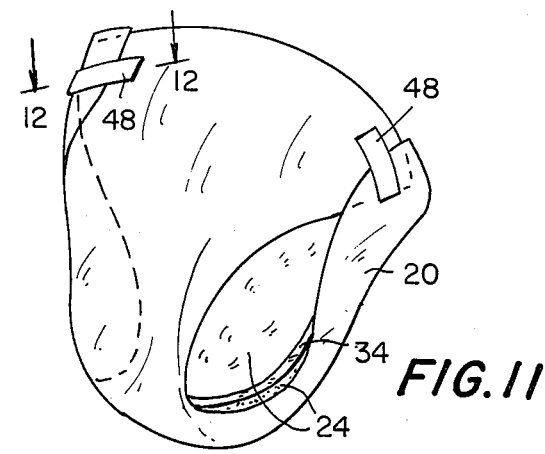
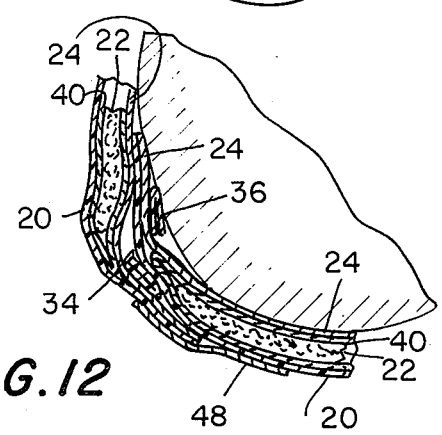

DISPOSABLE DIAPER HAVING FRONT SIDE EDGE SEALING MEANS

BACKGROUND OF THE INVENTION

1. FIELD OF THE INVENTION

This invention relates generally to diapers and more particularly to an improved disposable diaper provided with sealing strips and to a method of manufacture thereof.

2. DESCRIPTION OF THE PRIOR ART

Conventional disposable diapers comprise a rectangular back sheet of waterproof material, a rectangular absorbent pad and a rectangular top sheet of hydrophobic material. The back sheet is generally wider than the pad and the top or face sheet and the longitudinal edges of the back sheet extend past the longitudinal edges of the pad and the top sheet. The back sheet is folded around the edges of the pad and onto the top sheet. The longitudinal edges of the back sheet are then adhered to the top sheet. Conventional disposable diapers are prepared in one of a number of prefolded configurations to permit the disposable diaper to have a narrowed portion in order to make the disposable diaper more closely adapted to fit the trunk and thighs of an infant that if the disposable diaper was applied in a non-prefolded rectangular configuration.

In order to successfully meet consumer expectations a disposable diaper must, as an assembly, have sufficient strength to prevent tearing when applied and when worn by an infant and must also have sufficient limpness or ability to be molded or adjusted by hand to fit closely around the thighs and trunk of an infant. This limpness, or ability to be molded or adjusted by hand, is required in order to create a seal to contain discharged urine in order to give the absorbent pad sufficient time to absorb the urine. Failure to provide these features results in a product which causes soiled clothing, infant discomfort and a general reaction on the part of the consumer that the product is not effective.

Present disposable diapers attempt to meet the above goal of having sufficient strength to avoid tearing by providing the above mentioned folded edge of back sheet on each of the longitudinal edges of the diaper. The back sheet on one form of conventional disposable diaper has two side flaps which are folded, one each, around the longitudinal edges of the absorbent pad and are fastened to the face sheet by adhesive. In this form of conventional disposable diaper the combined width of the two side flaps which are folded onto the top sheet are equal to approximately two thirds of the overall width of the diaper in the folded configuration. This double layer of back sheet material along the longitudinal edges of the diaper is required because the tensile forces created when applying a disposable diaper are sufficiently large so as to deform or tear the back sheet if a single layer back sheet is used at the longitudinal edges of the diaper. The folded portion of the back sheet are placed in a complex state of combined bending and tensile stress when the conventional disposable diaper is applied. This results in local buckling and bulging of the back sheet away from the thighs and trunk of the infant with consequent loss of sealing contact.

Another disadvantage of present conventional disposable diapers is that the folding of the back sheet over the edge of the absorbent pad prevents air from contacting the edge of the pad. The consequent thermal insulation of the edges of the pad by the back sheet contributes to the absorbent pad retaining the head produced by the absorption and accumulation of waste products and also retaining body heat. This heat retaining property of conventional disposable diapers is undesirable since it leads to infant discomfort. In addition to the undesireable effects in conventional disposable diapers related to the two portions of the back sheet which cover the longitudinal edges of the pad, additional undesirable effects are related to the side flap portions of the back sheet which overlay the face sheet. These portions of the backsheet contribute to the undesirable thermal insulating properties of the conventional disposable diaper. In addition, when the conventional disposable diaper is applied to an infant, the side flap portions form a relatively large portion of the overall width of the diaper in the narrow crotch area. The side flap portions prevent absorption of waste products through the hydrophobic face sheet in those covered areas and actually increase dripping of excess fluid. In addition, in the crotch area, those portions of the back sheet which overlay the top sheet, since they form a relatively large portion of the overall disposable diaper width, readily become wet with urine and cause infant discomfort. In certain cases these wet portions at the edges of the side flaps in contact with the infant's skin can lead to skin rashes and other skin disorders caused by the combined effects of urine and body heat.

A rectangular diaper is disclosed in the U.S. Pat. No. 3,592,194 issued to Robert C. Duncan on July 13, 1971 for DIAPER HAVING IMPROVED WICKING AND DRYNESS. This rectangular diaper is folded in a box pleat such as also disclosed in British Pat. No. 1,011,888 of Dec. 1, 1965. However, the panels defined by the box pleated diaper are spaced substantially from each other requiring that the central panel behind the pleated panels receive most of the urine while the spaced apart panels provided with side flaps also permit chaffing.

Further, in order to provide the desired absorptive capacity, the rectangular diaper with the spaced apart panels is of an undue width which allows the legs to force the diaper down so that it tends to sag away from the trunk of the body thus preventing proper utilization of the absorptive capabilities of the diaper.

In addition, in the prior art rectangular diapers because of the spaced-apart position of the folded panels of the diaper, surface wetness of the hydrophobic face sheet of the central portion or panel of the diaper resulting from the inefficient transfer of waste fluids from the center into the total mass of absorbent material is prevalent because of the space-apart position of the folded panels which results in a wetting of the face sheet adjacent the skin of the infant, thus reducing the advantages otherwise inherent in the use of a hydrophobic face sheet because instead of small areas which have been wet while permitting passage into the hydrophilic or absorbent pad, substantially the entire surface area of the hydrophobic sheet becomes wet and the chaffing on an infant is increased due to the wetness and the spaced-apart position of the folded panels.

OBJECTS OF THE INVENTION

It is an object of the present invention to provide a disposable diaper which includes an arrangement of parts for providing for improved surface dryness in the crotch area of the diaper and wherein the surface of the hydrophobic face sheet adjacent to the infant's skin is rendered less subject to flooding by fluids not yet absorbed or retained within the absorbent material.

Another object of the invention is to provide a narrower, more comfortable, and better fitting diaper in which the wicking of fluids is enhanced and a fluid seal is provided.

Yet another object of this invention resides in the provision of a method of manufacturing this improved diaper in a convenient manner.

An additional object of this invention to provide a disposable diaper having relatively high tensile strength in the longitudinal direction combined with relatively low transverse bending strength.

Another object of this invention is to provide a disposable diaper having increased flexibility of the longitudinal edges to facilitate the formation of a desirable tight fit to the leg and trunk of an infant.

A further object of this invention resides in the provision of a disposable diaper having a pair of sealing folds spaced inwardly of the longitudinal edges for increased sealing capability.

SUMMARY OF THE INVENTION

The concept of this invention features an improved disposable diaper having a rectangular waperproof back sheet, an absorbent pad narrower than the back sheet and centered on the back sheet, a hydrophobic face sheet equal in width to the back sheet and disposed in alignment with the back sheet and on top of the absorbent pad. The diaper is then box folded with inwardly extending panels being in abutting relationship.

These, together with the various ancillary objects and features of this invention, which will become apparent as the following description proceeds are attained by this disposable diaper preferred embodiments of which are illustrated in the accompanying drawing, by way of example only, wherein:

BRIEF DESCRIPTION OF THE DRAWINGS

FIG. 7 is a view showing schematically, a partially folded diaper constructed in accordance with the present invention;

FIG. 8 is a schematic view illustrating a completely folded diaper;

FIG. 9 is a top view of the folded diaper of FIG. 4 with one end fanned out in preparation for application to an infant and with parts broken away;

FIG. 10 is a perspective view illustrating the configuration of the disposable diaper in use;

FIG. 11 is another perspective view illustrating the configuration of the disposable diaper in use; and FIG. 12 is a fragmentary sectional view taken along the plane of the line 12—12 of FIG. 11.

DESCRIPTION OF THE PREFERRED EMBODIMENTS

Figure 1:
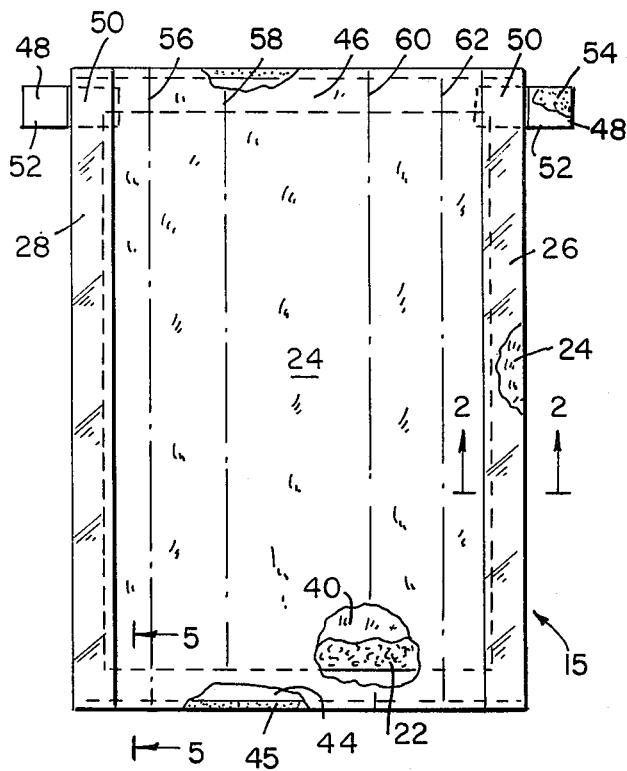
FIG. 1 is an overall plan view of a disposable diaper constructed in accordance with the concepts of the present invention prior to being folded.
Figure 3:
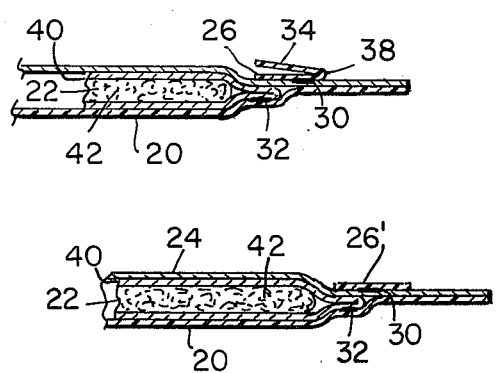
FIG. 3 is a fragmentary sectional view similar to FIG. 2 showing an alternative embodiment of the invention in which a longitudinal strip or side flap portion on top of the hydrophobic face sheet is inwardly folded.

With continuing reference to the accompanying drawing, wherein like reference numerals designate similar parts throughout the various views, reference numeral 15 is used to generally designate a disposable diaper constructed in accordance with the concepts of the present invention. The disposable diaper 15 includes a rectangular back or bottom sheet 20 made of a thin flexible plastic material such as polyethylene, polypropylene, or polyvinyl chloride hydrophillic. An absorbent pad 22, shorter in length and width than the bottom sheet 20 is centered on the back sheet 20 as is shown in FIG. 1. A face sheet 24 of hydrophobic material is disposed on top of the absorbent pad 22. The face sheet 24 is of less width than the back sheet 20 and of the same length and is aligned with the back sheet 20. The face sheet 24 may be made of paper or of a non-woven web having the desired properties of softness to touch, porosity and hydrophobic action with respect to fluids. The face sheet 24 is bonded to the back sheet 20 by suitable adhesive about the periphery of the pad 22. The excess width of the back sheet 20 is folded over the face sheet 24 to form side flaps 26 and 28. The use of hydrophobic material permits the passage of fluids from the outside of the disposable diaper 15 through the face sheet 24 and onto the absorbent pad 22 where the fluid is absorbed. The hydrophobic material reduces the area of wetness caused by fluids excreted by an infant as such pass to the absorbent pad 22 through the face sheet 24. As can be seen in FIG. 3, the side flaps 26 and 28 form longitudinal strips which are equal in length to the length of the face sheet 24 and are each approximately equal in width to the distance between the edge of the absorbent pad 22 and the edge of the face sheet 24. The longitudinal strips are entirely severed from the back sheet 20 by a cutting step using cutting blades. The longitudinal strips 26 and 28 are disposed on top of the face sheet 24 and are disposed, one each, between the longitudinal edges of the absorbent pad 22 and the longitudinal edges of the face sheet 24. The longitudinal strip 26 and 28, the top sheet 24, the absorbent pad 22, and the back sheet 20 are held in relative position by means of adhesive 30, 31 and 32. Adhesive 32 deposited in a narrow line between the absorbent pad 22 and the back sheet 20, adhesive 31 deposited in a narrow line between the absorbent pad 22 and the top sheet 24, and adhesive 30 deposited in a narrow line between the longitudinal strip 26 and the top sheet 24. The adhesive portions 30, 31 and 32 have been described with reference to the longitudinal edge of the disposable diaper on which longitudinal strip 26 is disposed. It is understood that similar adhesive portions are present on the longitudinal edge of the disposable diaper on which longitudinal strip 28 is disposed.

Figure 2:
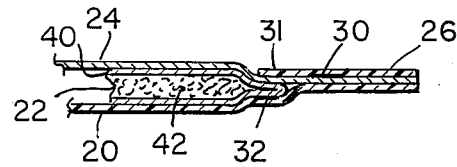
FIG. 2 is a fragmentary sectional view taken along the plane of the line 2—2 in FIG. 1.

The longitudinal strips 26 and 28 in the embodiment of FIGS. 1 and 2 are made of the same sheet of thin flexible plastic material as the back sheet 20. In the preferred method of manufacture of the disposable diaper according to the present invention the back or bottom sheet 20 in its original state is larger in width to the bottom sheet in the finished state having as shown in FIG. 1 plus the additional width of the side flaps from which the longitudinal strips 26 and 28 plus a small allowance for cutting or slitting, to be presently explained. In this method of manufacture, the back sheet 20 in its original state is deposited as a first step. A pair of narrow adhesive portions are deposited longitudinally on the bottom sheet, with one of such portions shown as adhesive 32 in FIG. 2. Absorbent pad 22 is deposited on top of the back sheet 20 and centered with respect to the longitudinal edges of the back sheet 20. A pair of narrow adhesive portions are deposited on the absorbent pad 22, with one of such portions shown as adhesive 31 in FIG. 2. Top sheet 24 is then deposited on top of the absorbent pad 22 and is centered with respect to the longitudinal edges of the back sheet 20. A pair of narrow adhesive portions are deposited longitudinally on the face sheet 24, with one of such portions shown as adhesive 30 in FIG. 2. Side flaps 26 and 28 of the back sheet 20 are then folded over on to the face sheet 24 and are adhered to the face sheet 24 by means of the narrow adhesive portions deposited on the face sheet 24. The two longitudinal edges of the back sheet 20 which curve around the longitudinal edges of the face sheet are then subjected to a slitting, trimming or cutting operation. This operation cuts longitudinal strips 26 and 28 free of the bottom sheet 20 and the disposable diaper then assumes the configuration shown in FIG. 2.

Figure 4:
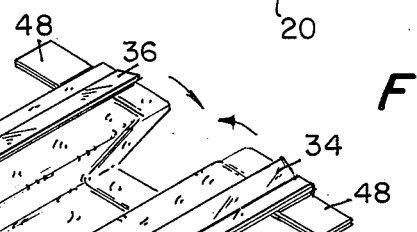
FIG. 4 is a sectional detail view similar to FIG. 2 of another modified form of the invention.

The slitting or trimming operation which produces the configuration of FIG. 1 and FIG. 2 results in a disposable diaper which has longitudinal edges with unexpected flexibility. This is a great advantage in applying the diaper to an infant and results in a neat appearance since the edge can be molded or shaped by hand to fit closely around the legs and trunk of the infant and this close fit helps retain urine and waste matter until it can be absorbed by the absorbent pad. In the embodiment shown in FIG. 4, the longitudinal strip 26 is formed by the additional cutting action of cutting along the fold 38 as shown in FIG. 3. Alternatively, the back sheet 20 can be made of the same width as the face sheet and the strip 26 separately applied.

The absorbent pad 22 has a porous outer layer 40 made of a porous paper, or non-woven web and an absorbent inner layer 42 made of cellulose wadding or the like. The outer layer 40 has a lateral dimension slightly greater than the lateral dimension of absorbent inner layer 42 and the adhesive 32 is positioned so as to contact the portion of the outer layer 40 which extends past the absorbent inner layer 42 as is shown in FIG. 2.

Figure 6:
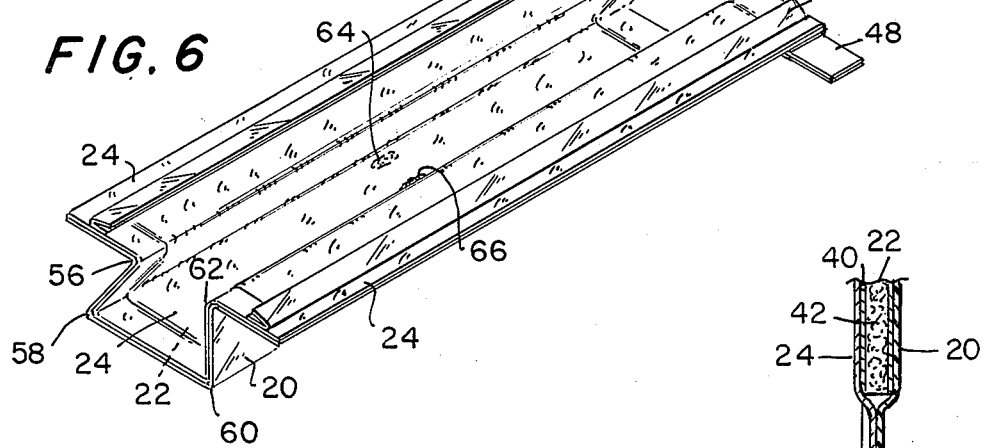
FIG. 6 is a perspective view of a partially folded disposable diaper constructed in accordance with the embodiment of FIG. 3.

In an alternative embodiment of the invention as shown in FIGS. 3 and 6, the longitudinal strips 26 and 28 are subjected to an additional manufacturing step comprising folding a portion of longitudinal strips 26 and 28 inward toward each other. The fold on longitudinal strip 26 is shown as fold 38 in FIG. 3. A sealing flap 34 is thus formed on longitudinal strip 26 as is shown in FIGS. 3 and 6. A similar sealing flap 36 is formed on longitudinal strip 28 as is shown in FIG. 6. The provision of the sealing flaps 34 and 36 results in several significant advantages. The provision of the sealing flaps 34 and 36 decreases the width of the longitudinal strip which is in contact with the infant's skin. This results in a cooler disposable diaper and a smaller area on the disposable diaper where a waterproof material is in contact with the infant's skin and consequently a smaller area where potential skin rashes and other disorders caused by the continued presence of urine in contact with the skin can occur. The provision of fold 38 on longitudinal strip 26 also increases the number of layers of flexible plastic sheet on the longitudinal edge of the disposable diaper from two layer as shown in FIG. 2 to three layers as shown in FIG. 3. In the application of a disposable diaper to an infant significant tension is placed along the longitudinal edges of the diaper in order to make the diaper fit closely around the legs of an infant. It is important to make the edges of the diaper fit closely in order to effect a mechanical seal to enable the diaper to retain urine and waste matter to give the absorbent pad sufficient time to absorb the urine and waste matter. The above mentioned tension is placed on the longitudinal edges by the fingertips which act on a relatively narrow area of the longitudinal strip 26. Although folding the longitudinal strip 26 does not increase the cross-sectional area of the longitudinal strip 26 it however increases the cross sectional area in the portion of longitudinal strip 26 which is grasped by the hand when the disposable diaper is applied. In other words, the folding of the longitudinal strip 26 into a double thickness narrow strip optimized the effectiveness of the cross-sectional area of the longitudinal strip 26. In addition, when the disposable diaper 15 in accordance with the present invention is placed on an infant, the sealing flaps 34 and 36 of the longitudinal strips 26 and 28, respectively, tend to flex slightly away from the top sheet 24. This creates two oppositely disposed trough like or channel like portions which act to retain urine and other waste matter.

The longitudinal dimension of the face sheet 24 is approximately equal to the longitudinal dimension of the back sheet 20 and the face sheet 24 is aligned longitudinally with the back sheet 20. The longitudinal dimension of the absorbent pad 22 is smaller than the longitudinal dimension of the face sheet 24 and the back sheet 20 and the absorbent pad is centered between the ends of the face sheet 20.

Figure 5:
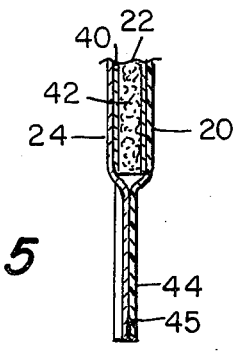
FIG. 5 is a fragmentary sectional view taken along the plane of the line 5—5 in FIG. 1.

The end portions of the face sheet 24 and the back sheet 20 are shown as flaps 44 and 46 in FIG. 1 and FIG. 5. A pair of narrow lines of adhesive, shown as adhesive 45 in FIG. 5, joins the top sheet 20 and the bottom sheet 24 within flaps 44 and 46. Flaps 44 and 46 have a dual function. When the disposable diaper 15 is applied to an infant, flaps 44 and 46 may be turned inward onto the face sheet 24 to provide a seal against leaking and wicking of waste matter out of the disposable diaper and onto the torso of the infant. When it is desired to dispose of the soiled diaper in a toilet, flap 44 or flap 46 can be grasped and the top sheet 24 peeled away from the back sheet 20 thus permitting solid waste matter to drop into the toilet and permitting the absorbent pad 22 to drop into the toilet while the waterproof back sheet 20 is held in the hand. The back sheet 20 is then disposed separately and is not flushed down the toilet.

A pair of pressure sensitive tape fasteners 48 are provided on one end of back sheet 20. The fasteners 48 each comprise a strip of pressure sensitive tape divided into a first area 50 in which the tape fastener is adhered to back sheet 20 and a second area in which the tape fastener adhesive film is covered by a release tab 52. Release tabs 52 can be readily peeled away from the adhesive film after the disposable diaper is applied to an infant thus revealing the adhesive film portion 54 and the tape fasteners 48 can be used to secure the ends of the disposable diaper 15 as shown in FIG. 10 and FIG. 11.

The disposable diaper 15 according to the present invention is provided in a pre-folded configuration shown in FIG. 8. This pre-folded configuration is accomplished through the use of longitudinal and parallel folds 56, 58, 60 and 62 shown in FIG. 1. The disposable diaper 15 is folded inwardly along the folds 58 and 60 as is shown in FIG. 6 and FIG. 7 and the disposable diaper 15 is folded outwardly along the folds 56 and 62 as is also shown in FIG. 6 and FIG. 7. The folds 56, 58, 60 and 62 are disposed so that when in the pre-folded condition, shown in FIG. 8, the folds 56 and 62 are touching. This configuration provides a narrowed portion in the crotch area combined with increased thickness in this area when the disposable diaper is applied to an infant. The narrowed portion of the diaper leads to increased infant comfort and improved appearance while the increased thickness leads to increased absorptive capacity. When the disposable diaper 15 is about to be applied to an infant one end is fanned out by gently opening the folds 56, 58, 60 and 62 along approximately one half the length of the disposable diaper 15 as is shown in FIG. 9. Adhesive spots 64 and 66 are provided on the face sheet 24 approximately centered along the length of the disposable diaper 15 and are disposed to adhere the portion of the disposable diaper between the folds 56 and 58 and the portion of the disposable diaper between the folds 60 and 62 each onto the portion of the disposable diaper between the folds 58 and 60. Adhesive spots 64 and 66 assist in unfolding the pre-folded disposable diaper to the configuration shown in FIG. 9. After the disposable diaper 15 is unfolded into the configuration shown in FIG. 9, the infant is placed on the disposable diaper 15 with his buttocks slightly closer to the fanned out end and the unfanned out end is brought up between his legs and also fanned out. The opposite ends of the disposable diaper 15 are then brought together and the tape fasteners 48 are used to secure the ends of the disposable diaper 15 to each other as is shown in FIGS. 10, 11 and 12.

A latitude of modification, substitution and change is intended in the foregoing disclosure and in some instances, some features of the invention will be employed without a corresponding use of other features.

What is claimed is:

1. A disposable diaper comprising a waterproof back sheet, a hydrophobic face sheet, and an absorbent pad sandwiched between said back sheet and said face sheet, said back sheet, said face sheet and said pad being formed into a box pleated configuration in at least the crotch region thereof by means of a plurality of longitudinal folds, said longitudinal folds defining opposed portions extending inwardly into abutting relationship, said pad being of less width than said face sheet and said back sheet, said face sheet being of substantially the same width as said back sheet, and sealing strips of water proof material separate from a said back sheet secured on said face sheet parallel to the side edges thereof in at least the crotch area.

2. A disposable diaper according to claim 1, wherein said pad is smaller in length that said back sheet and said face sheet so that said back sheet and said face sheet abut each other about the periphery of said pad, and adhesive means securing said face sheet to said back sheet outwardly of the periphery of said pad.

3. A disposable diaper comprising a waterproof back sheet, an absorbent pad overlying said back sheet, and a hydrophobic face sheet overlying said pad, said back sheet, said face sheet and said pad having a plurality of longitudinal folds, said longitudinal folds defining a central panel opposed inwardly extending panels overlying said central panel, and opposed outwardly extending panels overlying said inwardly extending panels, the innermost edges of said inwardly extending panels being in abutting relationship, said pad being of less width than said face sheet and said back sheet; said face sheet being of substantially the same width as said back sheet, and sealing strips of waterproof material separate from said back sheet secured to said face sheet parallel to the side edges thereof in at least the crotch area.

4. A disposable diaper according to claim 3, wherein said central panel has a width substantially equal to the sum of the widths of said inwardly extending panels.

5. A disposable diaper according to claim 4, wherein the width of each inwardly extending panel is equal.

6. A disposable diaper comprising a rectangular back sheet, a rectangular absorbent pad having length and width dimensions smaller than corresponding length and width dimensions of said back sheet and disposed centered on said back sheet, a face sheet equal in length and width to said back sheet disposed on top of said absorbent pad and in alignment with said back sheet, a pair of longitudinal strips separate from said back sheet each having a length equal to the length of said back sheet and a width equal to the side distance between said absorbent pad and a longitudinal edge of said back sheet and with a longitudinal edge of each longitudinal strip aligned with a longitudinal edge of said face sheet and with said longitudinal strips disposed on top of said face sheet, and adhesive means disposed between adjacent portions of said longitudinal strips and said face sheet, adjacent portions of edges of said face sheet and said absorbent pad and adjacent portions of edges of said pad and said back sheet.

7. A disposable diaper according to claim 6, wherein said back sheet and said longitudinal strips are each made of thin waterproof plastic sheet material.

8. A disposable diaper according to claim 6, wherein said face sheet is made of a hydrophobic paper.

9. A disposable diaper according to claim 6, wherein said adhesive means comprises a narrow longitudinal line of adhesive.

10. A disposable diaper according to claim 6, wherein said disposable diaper is folded into a boxpleat configuration comprising a first pair of spaced apart parallel longitudinal folds disposed in a direction to bring adjacent surfaces of said face sheet into contact and a second pair of spaced apart parallel longitudinal folds disposed outwardly of said first pair of spaced apart parallel longitudinal folds and disposed to bring adjacent portions of said back sheet into contact.

11. A disposable diaper according to claim 6, wherein said folds are disposed to bring said second set of spaced apart parallel longitudinal folds into contact with each other.

12. A disposable diaper according to claim 6, wherein said longitudinal strips each have a longitudinal fold disposed facing said respective longitudinal edge of said face sheet and with said folded portion of said longitudinal strips folded inwardly and disposed on top of the portion of said longitudinal strip adhesively secured to said face sheet.

13. A disposable diaper according to claim 12, wherein said longitudinal fold on said longitudinal strip divides said longitudinal strip into two equal portions.

14. A method of making a disposable diaper comprising the steps of sandwiching a hydrophilic material between a waterproof back sheet and a hydrophobic face sheet, said pad being of less width than said back sheet, said face sheet being of greater width than said pad but less than said back sheet, said pad being smaller in length than said back sheet and said face sheet, folding the excess width of said back sheet over said face sheet forming side flap portions, bonding said side flap portions to said face sheet, and then cutting said side flap portions free of said back sheet to form a fluid seal on the diaper face.

15. A method according to claim 6, including the step of folding said severed side flap portions inwardly toward the center of the diaper to form fluid catching seals.

16. A method according to claim 14, including thereafter folding said diaper in a boxpleat with the folded portions abutting each other.

17. A method according to claim 15, including the step of bonding said face sheet to said back sheet about the periphery of said pad.

18. A method according to claim 14, including the steps of folding said severed side flap portions inwardly toward the center of the diaper to form fluid catching seals, and thereafter folding said diaper in a boxpleat with the folded portions abutting each other.

19. A method according to claim 14, wherein said diaper is folded so that said folded portions abut each other along the center line of said diaper.

* * * * *